(12) United States Patent
Wysopal

(10) Patent No.: US 11,076,991 B2
(45) Date of Patent: Aug. 3, 2021

(54) LOW VOLTAGE COMMUNICATION BETWEEN SUBSYSTEMS IN A LASER EYE SURGERY SYSTEM

(71) Applicant: AMO DEVELOPMENT, LLC, Santa Ana, CA (US)

(72) Inventor: Jan C. Wysopal, Livermore, CA (US)

(73) Assignee: AMO Development, LLC, Santa Ana, CA (US)

( * ) Notice: Subject to any disclaimer, the term of this patent is extended or adjusted under 35 U.S.C. 154(b) by 55 days.

(21) Appl. No.: 16/403,450

(22) Filed: May 3, 2019

(65) Prior Publication Data

US 2019/0254869 A1 Aug. 22, 2019

Related U.S. Application Data

(62) Division of application No. 14/069,098, filed on Oct. 31, 2013, now Pat. No. 10,278,862.

(60) Provisional application No. 61/721,726, filed on Nov. 2, 2012.

(51) Int. Cl.
*A61F 9/008* (2006.01)

(52) U.S. Cl.
CPC .... *A61F 9/008* (2013.01); *A61F 2009/00844* (2013.01)

(58) Field of Classification Search
CPC ............... A61F 9/008; A61F 2009/00844
USPC ........................................................ 606/4
See application file for complete search history.

(56) References Cited

U.S. PATENT DOCUMENTS

| 5,459,570 A | 10/1995 | Swanson et al. |
| 5,748,352 A | 5/1998 | Hattori |
| 5,748,898 A | 5/1998 | Ueda |
| 6,053,613 A | 4/2000 | Wei et al. |
| 6,111,645 A | 8/2000 | Tearney et al. |
| 6,836,290 B1 * | 12/2004 | Chung .................... H04N 5/335 348/294 |
| 2006/0058682 A1 * | 3/2006 | Miller ................ G01B 9/02068 600/476 |
| 2009/0118794 A1 | 5/2009 | McClure et al. |

* cited by examiner

*Primary Examiner* — Aaron F Roane
(74) *Attorney, Agent, or Firm* — Johnson & Johnson Surgical Vision, Inc.

(57) ABSTRACT

A laser eye surgery system comprises subsystems which communicate with one another through low voltage differential signaling (LVDS). The laser eye surgery system may comprise a first subsystem interface, including an LVDS driver or transmitter coupled to and in communication with an LVDS receiver of a first subsystem of the laser eye surgery system. The first laser eye surgery subsystem itself may comprise an LVDS transmitter coupled to and in communication with an LVDS receiver to return data to the first subsystem. Further laser eye surgery subsystems may also include the same arrangement of drivers and receivers with respective subsystem interfaces. LVDS lowers power consumption and the risk of error in communication between laser eye surgery systems, leading to safer and more reliable surgical procedures performed.

5 Claims, 5 Drawing Sheets

LOW VOLTAGE COMMUNICATION BETWEEN SUBSYSTEMS IN A LASER EYE SURGERY SYSTEM

CROSS-REFERENCE TO RELATED APPLICATIONS

This application is a divisional of and claims priority to U.S. patent application Ser. No. 14/069,098, filed Oct. 31, 2013, which is a non-provisional application of and claims the benefit of priority to U.S. Provisional Application No. 61/721,726, filed Nov. 2, 2012.

BACKGROUND

The present disclosure relates generally to surgical systems and in particular automated and computerized surgical systems. Although specific reference is made to laser eye surgery systems, the methods and apparatus described herein can be used with many different automated surgical systems for a variety of surgical procedures.

Many surgical procedures can be performed on patients, including ophthalmic surgery. Opthalmic surgery can include surgery on one or more of the cornea, the lens or the retina, for example.

Cataract extraction is a frequently performed surgical procedure. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). An estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Cataract surgery is typically performed using a technique termed phacoemulsification in which an ultrasonic tip with associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule. Access to the lens nucleus can also be provided by performing a manual continuous curvilinear capsulorhexis (CCC) procedure. After removal of the lens nucleus, a synthetic foldable intraocular lens (IOL) can be inserted into the remaining lens capsule of the eye. Typically, the IOL is held in place by the edges of the anterior capsule and the capsular bag. The IOL may also be held by the posterior capsule, either alone or in unison with the anterior capsule. This latter configuration is known in the field as a "Bag-in-Lens" implant.

One of the most technically challenging and critical steps in the cataract extraction procedure is providing access to the lens nucleus. The manual continuous curvilinear capsulorhexis (CCC) procedure evolved from an earlier technique termed can-opener capsulotomy in which a sharp needle was used to perforate the anterior lens capsule in a circular fashion followed by the removal of a circular fragment of lens capsule typically in the range of 5-8 mm in diameter. The smaller the capsulotomy, the more difficult it is to produce manually. The capsulotomy provides access for the next step of nuclear sculpting by phacoemulsification. Due to a variety of complications associated with the initial can-opener technique, attempts were made by leading experts in the field to develop a better technique for removal of the circular fragment of the anterior lens capsule prior to the emulsification step.

The desired outcome of the manual continuous curvilinear capsulorhexis is to provide a smooth continuous circular opening through which not only the phacoemulsification of the nucleus can be performed safely and easily, but also to provide for easy insertion of the intraocular lens. The resulting opening in the anterior lens capsule provides access for tool insertion during removal of the nucleus and for IOL insertion, a permanent aperture for transmission of the image to the retina of the patient, and also support of the IOL inside the remaining lens capsule that limits the potential for dislocation. The resulting reliance on the shape, symmetry, uniformity, and strength of the remaining lens capsule to contain, constrain, position, and maintain the IOL in the patient's eye limits the placement accuracy of the IOL, both initially and over time. Subsequently, a patient's refractive outcome and resultant visual acuity are less deterministic and intrinsically sub-optimal due to the IOL placement uncertainty. This is especially true for astigmatism correcting ("toric") and accommodating ("presbyopic") IOLs.

Problems may also develop related to inability of the surgeon to adequately visualize the lens capsule due to lack of red reflex, to grasp the lens capsule with sufficient security, and to tear a smooth circular opening in the lens capsule of the appropriate size and in the correct location without creating radial rips and extensions. Also present are technical difficulties related to maintenance of the depth of the anterior chamber depth after opening the lens capsule, small pupils, or the absence of a red reflex due to the lens opacity. Some of the problems with visualization can be minimized through the use of dyes such as methylene blue or indocyanine green. Additional complications may also arise in patients with weak zonules (typically older patients) and very young children that have very soft and elastic lens capsules, which are very difficult to controllably and reliably rupture and tear.

The implantation of a "Bag-in-Lens" IOL typically uses anterior and posterior openings in the lens capsule of the same size. Manually creating matching anterior and posterior capsulotomies for the "Bag-in-Lens" configuration, however, is particularly difficult.

Many patients have astigmatic visual errors. Astigmatism can occur when the corneal curvature is unequal in two or more directions. In Astigmatic Keratotomy, Corneal Relaxing Incision (CRI), and Limbal Relaxing Incision (LRI), corneal incisions are made in a well-defined manner and depth to allow the cornea to change shape to become more spherical. These corneal incisions can accomplished manually but often with limited precision.

Although prior laser eye surgical systems have been designed to overcome some of the above challenges, these prior surgery systems may be less than ideal in at least some respects and can provide less than ideal results in at least some instances. Although the prior laser eye surgery systems have attempted to automate laser corneal incisions and provide visualization of the eye, such systems can be somewhat cumbersome and more complex than would be ideal. For example, the prior laser eye surgery systems may comprise several subsystems that communicate and coordinate with each other and can be susceptible to noise and crosstalk in at least some instances. Also, the power consumption and size of these systems may also be greater than would be ideal in at least some instances, such that improved laser eye surgery may not be available to many people who could benefit from the therapies provided by these systems.

In many prior laser surgery systems, the effectiveness of the signaling can be dependent on the length of the signaling wire and its capacitance, and proximity to other wires, such that the signaling can be susceptible to noise and cross talk. Noise, crosstalk, and other electronic signaling defects may lead to errors and miscommunications between subsystems in at least some instances, and can reduce the safety, reliability, and precision of the surgical system and procedures the system performs, such that the outcome of the surgical procedure may be less than ideal.

Thus, improved surgical systems with improved communications between its subsystems are desired so that laser eye surgery procedures can be more reliably and safely performed and available to more patients.

SUMMARY

Improved systems and methods for communication between subsystems of a laser eye surgery system are provided. Such subsystems may include, but are not limited to, a patient interface control subsystem, a vacuum subsystem for controlled coupling of a patient interface with an eye of the patient, a ranging subsystem for tracking an eye of the patient, a laser surgery subsystem for operating a surgical laser, a laser interface subsystem for controlling the laser beam from the surgical laser, a power distribution subsystem, or various subsystems of the aforementioned subsystems themselves, and combinations thereof. One or more of these subsystems can communicate with another subsystem or subsystem interfaces using low voltage differential signaling (hereinafter "LVDS"). In low voltage differential signaling, electronic signals may be transmitted over a pair of signaling lines comprising a differential pair. Signaling will typically be bidirectional. One subsystem may comprise an LVDS driver and an LVDS receiver in communication through a differential pair with an LVDS receiver and an LVDS driver, respectively, of another subsystem. The low voltage data signals themselves may either be analog or digital. By using low voltage differential signaling, common-mode noise can be rejected, reducing the risks of noise-related problems such as crosstalk from neighboring lines. As a result, the surgical lines can use a much lower voltage, leading to lower overall power consumption.

The use of low voltage differential signaling can also result in a reduced amount of noise emission, which can allow the laser system to be more robust so that more people can receive the benefits of the surgical procedures provided by the system. The two lines of a differential pair can be in proximity to one another and create opposing electromagnetic fields which cancel each other. The strength of these fields can also be proportional to the flow of current through a line. Because LVDS provides a low current, a weak electromagnetic field is produced which provides reduced noise and decreases system complexity.

In a first aspect, a laser surgery system is provided. The laser surgery system comprises a first subsystem and a first interface for controlling the first subsystem. The first subsystem comprises control electronics in communication with the first interface. The first interface communicates with the first subsystem control electronics with low voltage differential signaling (LVDS).

In many embodiments, the laser eye surgery system further comprises a second subsystem and a second interface for controlling the second subsystem. The second subsystem comprises control electronics in communication with the second interface. The second interface communicates with the second subsystem control electronics with low voltage differential signaling.

Generally, the first interface will comprise a first LVDS transmitter and a first interface LVDS receiver. The control electronics of the first subsystem will comprise a first control electronics LVDS transmitter and a first control electronics LVDS receiver. The first interface LVDS transmitter is in communication with the first control electronics LVDS receiver. The first interface LVDS receiver is in communication with the first control electronics LVDS transmitter.

The first subsystem may comprise a vacuum subsystem, a ranging subsystem, a laser subsystem, a laser interface subsystem, a power distribution subsystem, a patient interface subsystem, an XY-scanning subsystem, or various subsystems of the aforementioned subsystems themselves, and combinations thereof. The ranging subsystem may comprise an OCT imaging device. The laser interface subsystem may comprise laser shutters and attenuators and may interface with the laser pulses from the laser subsystem as well as other elements in the optical path.

In many embodiments, the laser eye surgery system comprises a plurality of subsystems. Each subsystem of the plurality of subsystems, except for the power distribution subsystem, may communicate with at least one other subsystem through low voltage differential signaling (LVDS). The plurality of subsystems may comprise a vacuum subsystem, a ranging subsystem, a laser subsystem, a patient interface subsystem, a XY-scanning subsystem, various subsystems of the aforementioned subsystems themselves, and combinations thereof and each subsystem of the plurality of subsystems may communicate with at least one other subsystem using low voltage differential signaling (LVDS). In some embodiments, the power distribution subsystem may also communicate with at least one other subsystem provided that the power distribution subsystem is close enough in physical proximity to the main control electronics of the laser eye surgery system.

In another aspect, a method of communicating between subsystems of a laser eye surgery system is provided. A first subsystem of a laser eye surgery system is provided. The first subsystem comprises control electronics. A first interface for controlling the first subsystem is provided. The first interface is coupled to the control electronics of the first subsystem. Data is transmitted from the first interface to the control electronics of the first subsystem through a first low voltage differential signal. Data is transmitted from the control electronics of the first subsystem to the first interface through a second low voltage differential signal.

In many embodiments, a second subsystem of a laser eye surgery system is provided. The second subsystem comprises control electronics. A second interface for controlling the second subsystem is provided. The second interface is coupled to the control electronics of the second subsystem. Data is transmitted from the second interface to the control electronics of the second subsystem with a third low voltage differential signal. Data is transmitted from the control electronics of the second subsystem to the second interface with a fourth low voltage differential signal.

The first subsystem may comprise a vacuum subsystem, a ranging subsystem, a laser subsystem, a laser interface subsystem, a power distribution subsystem, a patient interface subsystem, an XY-scanning subsystem, a subsystem of the aforementioned subsystems themselves, or a combination thereof. The ranging subsystem may comprise an OCT imaging device. The vacuum subsystem, the ranging subsystem, the laser subsystem, the laser interface subsystem, the power distribution subsystem, the patient interface subsystem, and the XY-scanning subsystem may transmit bidirectional low voltage differential signals to each other.

The safety, reliability, and precision of laser eye surgery systems may also be improved by using other forms of low-power, low-noise signaling. For example, one or more of the subsystem of the laser eye surgery system may communicate with each other using low-power, low-noise analog data signaling.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Methods and systems related to laser eye surgery are disclosed. A laser is used to form precise incisions in the cornea, in the lens capsule, and/or in the crystalline lens nucleus, for example. A laser eye surgery system according to many embodiments will comprise a plurality of subsystems. One or more of these subsystems will be in communication with other subsystems or subsystem interfaces through low voltage differential signaling (LVDS), resulting in reduced noise and therefore overall increased system reliability.

System Configuration

Figure 1:
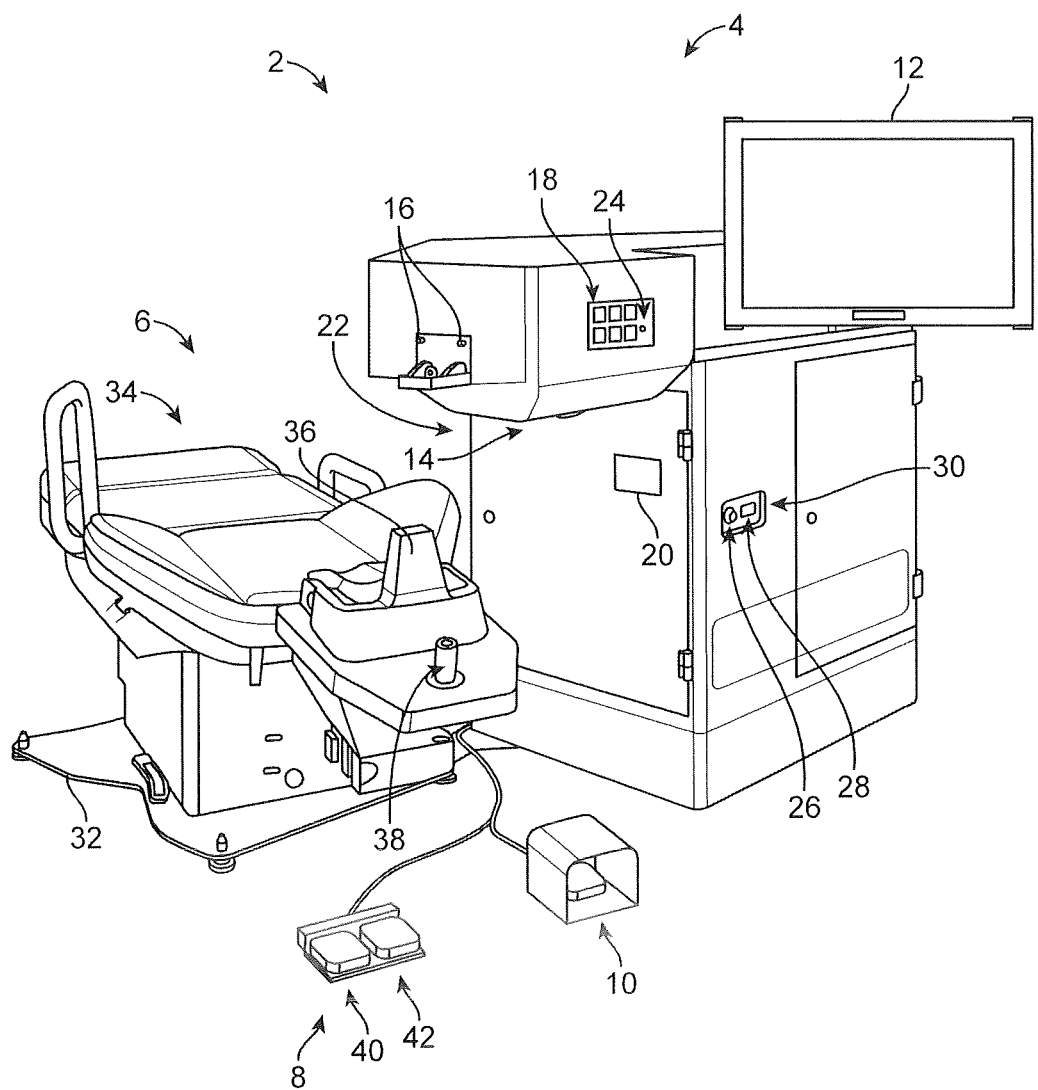
FIG. 1 is a perspective view showing a laser eye surgery system, in accordance with many embodiments.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38. To further protect against unintended chair motion, power supplied to the patient chair 6 may automatically be cut off using a switch.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user is without access to network based printing.

Figure 2:
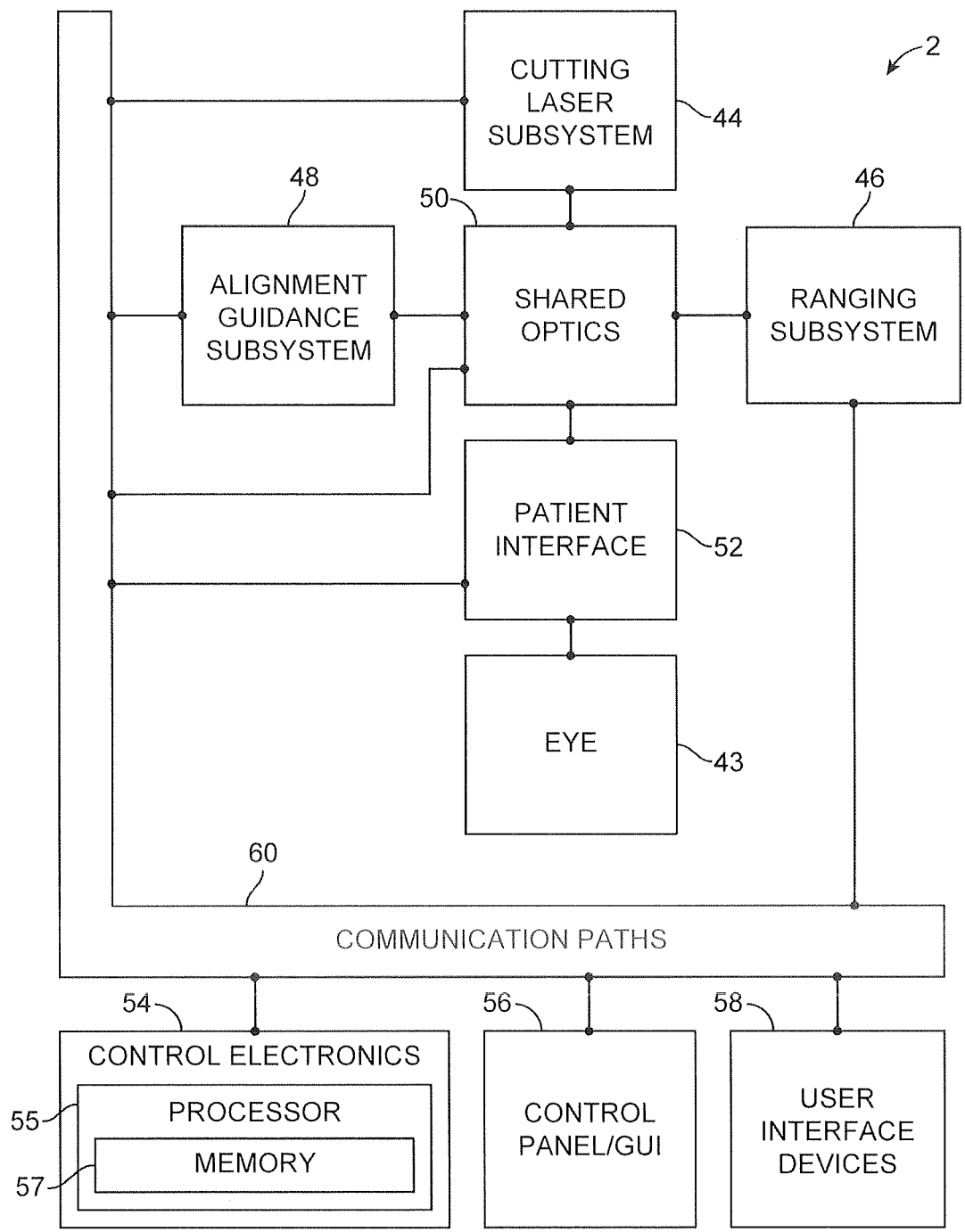
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, the ranging subsystem 46, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
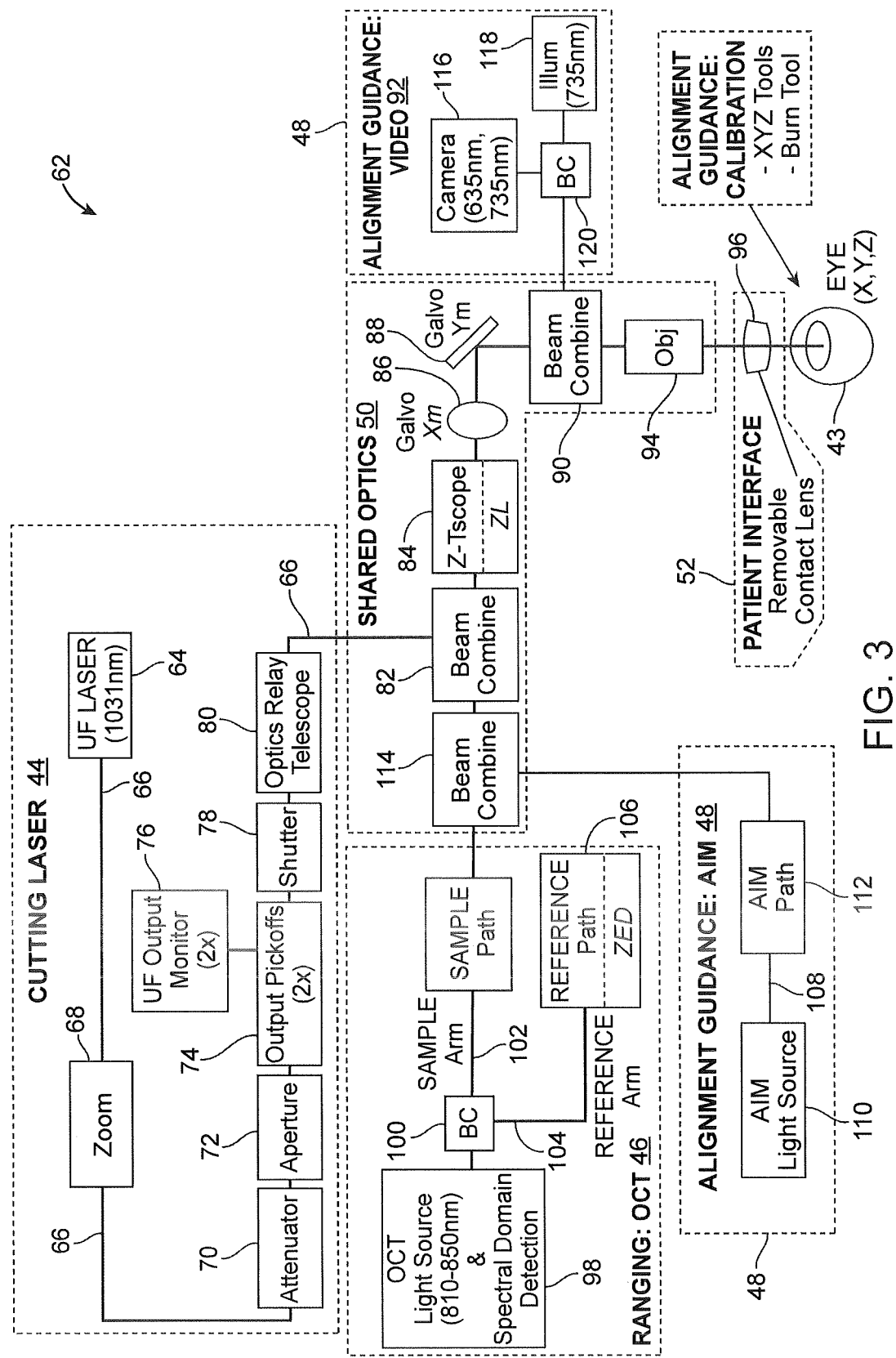
FIG. 3 is a simplified block diagram illustrating the configuration of an optical assembly of a laser eye surgery system, in accordance with many embodiments.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED, 106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc, are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source maybe be used as a fixation beam for the patient. The illumination may also be used to illuminate the patients pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be an suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 4:
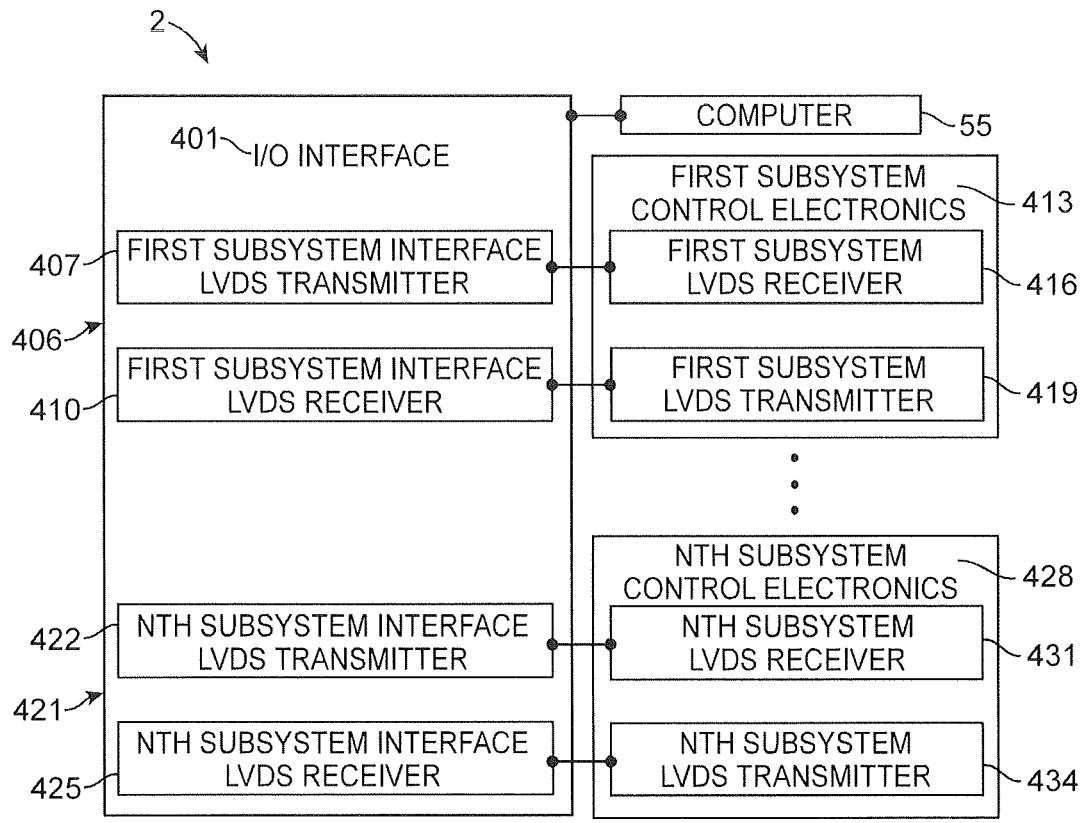
FIG. 4 is a simplified block diagram illustrating the communication between subsystems of a laser eye surgery system, in accordance with many embodiments.

FIG. 4 is a simplified block diagram illustrating communication between subsystems of a laser eye surgery system 2, in accordance with many embodiments. The laser eye surgery system 2 comprises an I/O interface 401 coupled to a processor, controller, or computer 55 described above. The I/O interface 401 comprises one or more subsystem interfaces, including a first subsystem interface 406. The first subsystem interface 406 comprises a first subsystem interface low voltage differential signaling (LVDS) driver or transmitter 407 and a first subsystem interface low voltage differential signaling (LVDS) receiver 410. The laser eye surgery system 2 further comprises a first subsystem having first subsystem control electronics 413 which comprises a first subsystem LVDS receiver 416 and a first subsystem LVDS transmitter 419. The first subsystem interface LVDS transmitter 407 is coupled to and communicates with the first subsystem LVDS receiver 416 via low voltage differential signaling. The first subsystem interface LVDS receiver communicates with the first subsystem LVDS transmitter 419 via low voltage differential signaling. The first subsystem interface 406 is thus coupled to the first subsystem control electronics 413 for controlling the first subsystem and receiving data therefrom. The first subsystem may be any one of the subsystems described herein, including but not limited to a vacuum subsystem, a ranging subsystem, a laser subsystem, a laser interface subsystem (for example, an ultrafast laser interface or control subsystem), a power distribution subsystem, a patient interface subsystem, an XY-scanning subsystem, or any further subsystem thereof.

The first subsystem interface LVDS driver or transmitter 407 and the first subsystem LVDS driver or transmitter 419 may comprise a commercially available high-speed differential line driver, such as an SN65LVDS387, SN75LVDS387, SN65LVDS389, SN75LVDS389, SN65LVDS391, or SN75LVDS391 high-speed differential line driver, commercially available from Texas Instruments Inc. of Dallas, Tex., for example. The first subsystem interface LVDS receiver 410 and the first subsystem LVDS receiver 416 may comprise a commercially available high-speed differential line receiver, such as an SN65LVDS386/388A/390, SN65LVDT386/388A/390, SN75LVDS386/388A/390, or SN75LVDT386/388A/390 high-speed differential line receiver commercially available from Texas Instruments Inc. of Dallas, Tex., for example.

The laser eye surgery system 2 may further comprise other subsystems, for example, up to an Nth subsystem 421 as shown in FIG. 4. The Nth subsystem interface 406 comprises an Nth subsystem interface low voltage differential signaling (LVDS) driver or transmitter 422 and an Nth subsystem interface low voltage differential signaling (LVDS) receiver 425. The laser eye surgery system 400 further comprises an Nth subsystem having Nth subsystem control electronics 428 which comprises an Nth subsystem LVDS receiver 431 and an Nth subsystem LVDS transmitter 434. The Nth subsystem interface LVDS transmitter 425 is coupled to and communicates with the Nth subsystem LVDS receiver 434 via low voltage differential signaling. The Nth subsystem interface LVDS receiver 425 communicates with the Nth subsystem LVDS transmitter 434 via low voltage differential signaling. The Nth subsystem interface 421 is thus coupled to the Nth subsystem control electronics 428 for controlling the Nth subsystem and receiving data therefrom. The Nth subsystem may be any one of the subsystems described herein, including but not limited to a vacuum subsystem, a ranging subsystem, a laser subsystem, a power distribution subsystem, a patient interface subsystem, an XY-scanning subsystem, or any further subsystem thereof.

The Nth subsystem interface LVDS driver or transmitter 422 and the first subsystem LVDS driver or transmitter 434 may comprise a commercially available high-speed differential line driver, such as an SN65LVDS387, SN75LVDS387, SN65LVDS389, SN75LVDS389, SN65LVDS391, or SN75LVDS391 high-speed differential line driver from Texas Instruments Inc. of Dallas, Tex. The Nth subsystem interface LVDS receiver 425 and the Nth subsystem LVDS receiver 431 may comprise a commercially available high-speed differential line receiver, such as an SN65LVDS386/388A/390, SN65LVDT386/388A/390, SN75LVDS386/388A/390, or SN75LVDT386/388A/390 high-speed differential line receiver from Texas Instruments Inc. of Dallas, Tex.

Figure 5:
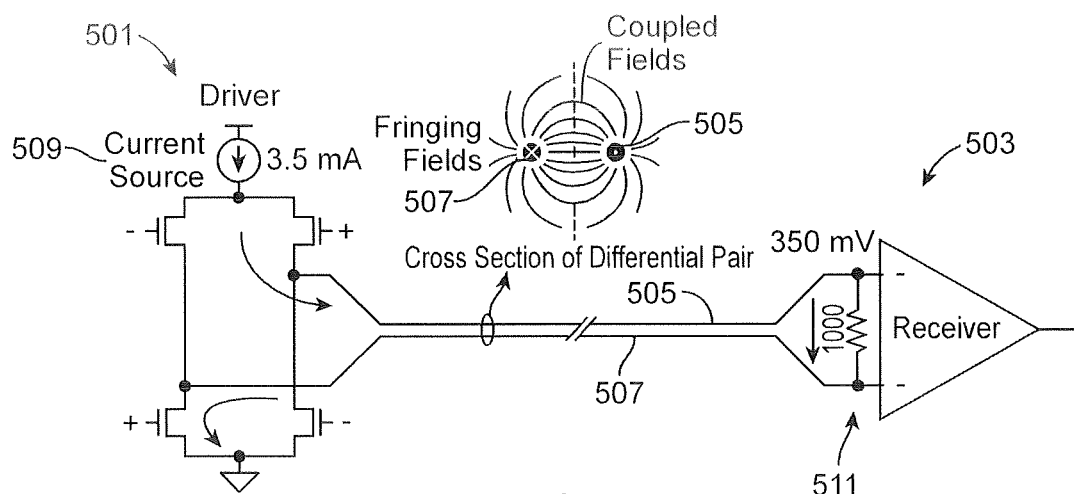
FIG. 5 shows circuitry of a differential pair used for low voltage differential signaling in a laser eye surgery system, in accordance with many embodiments.

FIG. 5 shows circuitry of a differential pair used for low voltage differential signaling in a laser eye surgery system 2, in accordance with many embodiments. In particular, FIG. 5 shows the coupling between an LVDS driver or transmitter 501 and an LVDS receiver 503. The LVDS driver 501 may comprise a commercially available driver described above and the LVDS receiver 503 may comprise a commercially available receiver described above. The driver 501 is coupled to the receiver 503 through a differential pair or a pair of parallel wires comprising a first wire 505 and a second wire 507. A cross section of the first wire 505 and the second wire 507 is also shown by FIG. 5. As shown in the cross-section, the two lines of a differential pair 505, 507 are adjacent to one another. When the lines 505, 507 transmit data, current flows in these two lines 505, 507 in equal and opposite directions. These current flows create electromagnetic fields which may couple to each other and will often be equal and opposite to each other, cancelling the electromagnetic fields out thereby limiting the amount of noise created.

A current source 509 can provide a constant 3.5 mA of current through the differential pair. The LVDS receiver 503 comprises a 100Ω resistor or load 511 through which this current is driven through, resulting in a power consumption of 1.2 mW. Another differential data transmission technology, RS-422, dissipates significantly more power at the receiver load—90 mW. Other differential signaling technologies such as RS485, ECL, and PECL, also dissipate significantly more power than LVDS.

Figure 6:
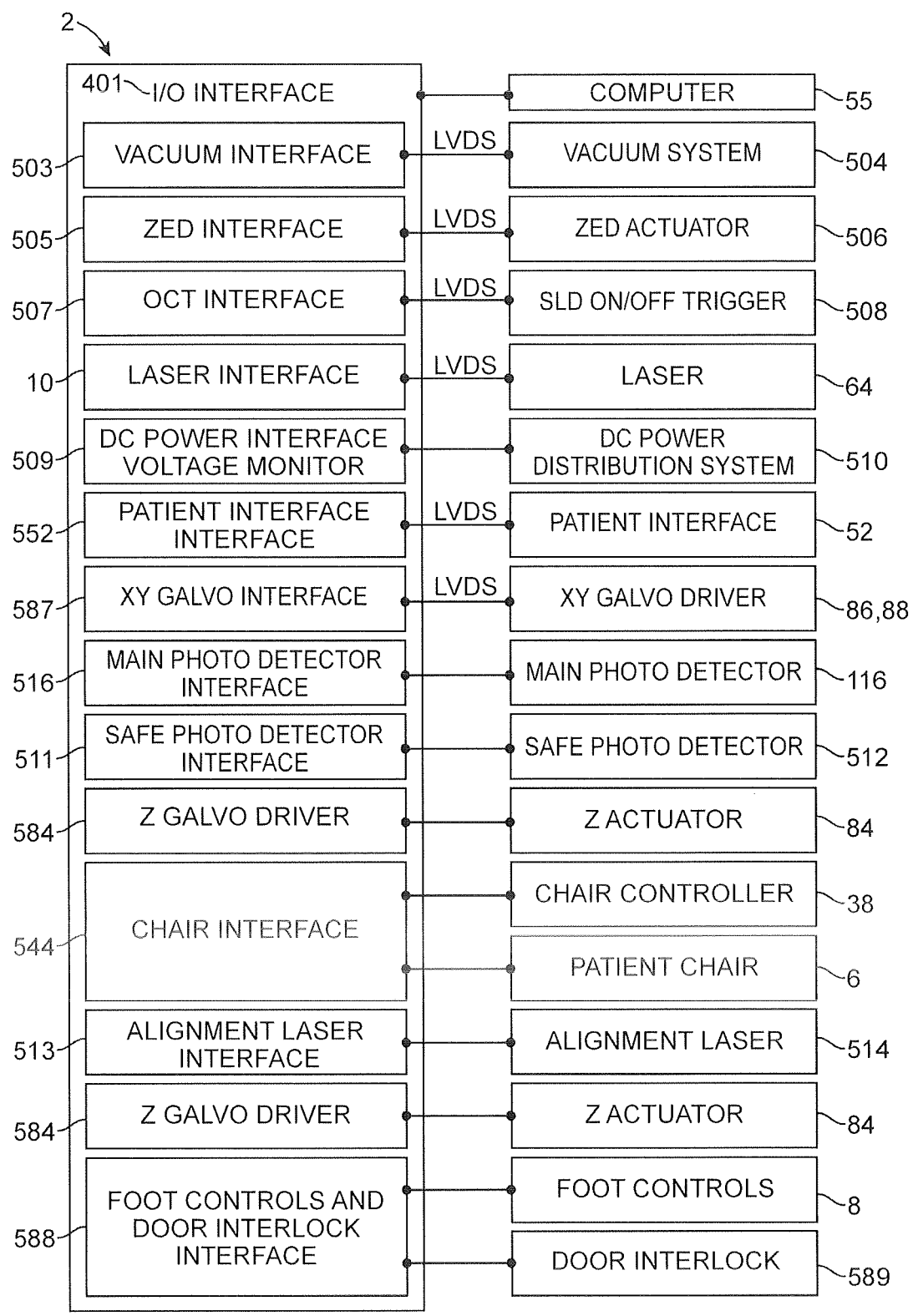
FIG. 6 is a simplified block diagram illustrating the communication between subsystems of a laser eye surgery system, in accordance with many embodiments.

FIG. 6 is a simplified block diagram illustrating the communication between subsystems of a laser eye surgery system 2, in accordance with many embodiments. The laser eye surgery system 2 comprises a processor, controller, or computer 55 coupled to an I/O interface 401. As discussed above with regard to FIG. 4, the I/O interface 401 may comprise a plurality of laser eye surgery subsystem interfaces. As shown in FIG. 6, the I/O interface 401 may comprise a vacuum interface 503 for controlling a vacuum subsystem for controlled coupling of a patient interface with an eye of the patient; a ZED interface 505 for adjusting the scanning depth of the ranging subsystem 46; an OCT interface 507 for controlling the ranging subsystem 46; laser interfaces 10; DC power interfaces or voltage monitor 509; an interface 552 for the patient interface 52; an XY galvo interface 587 for adjusting the lateral position of the UF laser 64; a main photo detector interface 516; a safe photo detector interface 511; a Z galvo interface 584 for adjusting the focus of the UF laser 64; a chair interface 533; alignment laser interface 513; and foot controls and door interlock interface 588.

These subsystems interfaces are coupled to and communicate with respective subsystems to control such subsystems and receive data therefrom. The vacuum interface 503 is coupled to the vacuum system 504. The ZED interface 505 is coupled to a ZED actuator 506 for adjusting the scanning depth of the ranging subsystem 46. The OCT interface 507 is coupled to a superluminescent diode (SLD) on/off trigger 508. The laser interfaces 10 are coupled to the UF laser 64 as well as to laser shutters and attenuators. The DC power interface voltage monitor 509 is coupled to a DC power distribution system 510. The patient interface interface 552 is coupled to the patient interface 52. The XY galvo interface 587 is coupled to X galvo driver or X-scan device 86 and Y galvo driver or Y-scan device 88. The main photo detector interface 516 is coupled to the main photo detector or camera 116. The safe photo detector interface 511 is coupled to a safe photo detector 512. The Z galvo driver 584 is coupled to a Z actuator or Z-telescope 84, which is operable to scan for focus position of the laser pulse beam 66. The chair interface 544 is coupled to the chair controller 38 and the patient chair 6 so that the position of the chair 6 can be displayed to and controlled by the user. The alignment laser interface 513 is coupled to an alignment laser 514 of the alignment guidance subsystem 48 described above. The foot controls and door interlock interface 588 is coupled to the foot controls 8 and the door interlock 589.

One or more subsystem interfaces will communicate with its respective subsystem through low voltage differential signaling (LVDS). As shown in FIG. 6, vacuum interface 503 and vacuum system 504 communicate with each other through LVDS; ZED interface 505 and ZED actuator 506 communicate with each other through LVDS; OCT interface 507 and SLD on/off trigger 508 communicate with each other through LVDS; laser interfaces 10 and laser 64 communicate with each other through LVDS; the patient interface interface 552 and patient interface 52 communicate with each other through LVDS; and the XY galvo interface 587 and XY galvo drivers 86, 88 communicate with each other through LVDS. While not shown in FIG. 6, other combinations or subsystems may also communicate with each other through LVDS. For instance, energy detectors such as main photo detector 116 and safe photo detector 512 may also communicate with main photo detector interface 516 and safe photo detector interface 511, respectively, as well as with a timing subsystem (not shown) through LVDS.

LVDS will be used for subsystems where low power consumption and/or low noise are desired, for example where the subsystem and subsystem interface are separated by a large distance or where one set of communication lines are in close proximity with another set of communication lines. In alternate embodiments, other low-power, low-noise signaling methods may be used alone or in combination. For example, any of the subsystems described herein communicating with one another through LVDS may instead or in combination use low-power, low-noise analog data signaling.

In some embodiments, all subsystems and subsystem interfaces communicate with each other through LVDS except the power distribution system because of the power distribution system's close proximity with the main, multifunction IO interface of the laser eye system 2 and the slow nature of control signals in general. In other embodiments where the power distribution system is in proximity with the main, multifunction IO interface, LVDS may be used. Often, LVDS will be used alongside other signal error protection schemes such as watchdog timers, handshaking protocols, and redundant circuits to increase overall system reliability.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of communicating between subsystems of a laser eye surgery system, comprising:
   providing a first subsystem including first subsystem control electronics;
   providing a processor;
   providing a first subsystem interface connected to the processor and connected to the first subsystem;
   providing bidirectional communication between the first subsystem interface and the first subsystem, including:
   by a first subsystem interface differential transmitter of the first subsystem interface, transmitting a first differential signal to the first subsystem for controlling the first subsystem;
   by a first subsystem interface differential receiver of the first subsystem interface, receiving data from the first subsystem via a second differential signal separate from the first differential signal;
   by a first subsystem differential receiver of the first subsystem control electronics, wherein the first subsystem differential receiver is separate from the first subsystem interface differential receiver and has a load, receiving from the first subsystem interface differential transmitter the first differential signal for controlling the first subsystem; and
   by a first subsystem differential transmitter of the first subsystem control electronics, wherein the first subsystem differential transmitter is separate from the first subsystem interface differential transmitter, transmitting the data to the first subsystem interface differential receiver via the second differential signal.

2. The method of claim 1 wherein the first subsystem comprises a vacuum subsystem, a ranging subsystem, a laser subsystem, a laser interface subsystem, a power distribution subsystem, a patient interface subsystem, or an XY-scanning subsystem.

3. The method of claim 2 wherein the ranging subsystem comprises an OCT imaging device.

4. The method of claim 2 further comprising: the vacuum subsystem, the ranging subsystem, the laser subsystem, the laser interface subsystem, the patient interface subsystem, and the XY-scanning subsystem transmitting bidirectional differential signals to each other.

5. The method of claim 1, further comprising:
   providing a second subsystem including second subsystem control electronics; and
   providing a second subsystem interface connected to the processor and connected to the second subsystem;
   by a second subsystem interface differential transmitter of the second subsystem interface, transmitting a third differential signal from the processor to the second subsystem for controlling the second subsystem;
   by a second subsystem interface differential receiver of the second subsystem interface, receiving second data from the second subsystem via a fourth differential signal;
   by a second subsystem differential receiver of the second subsystem control electronics, wherein the second subsystem differential receiver has a load, receiving from the second subsystem interface differential transmitter the third differential signal for controlling the second subsystem; and
   by a second subsystem differential transmitter of the second subsystem control electronics, transmitting the second data to the second subsystem interface differential receiver via the fourth differential signal.

* * * * *